United States Patent

Rempfler et al.

[11] Patent Number: 5,998,636
[45] Date of Patent: Dec. 7, 1999

[54] CARBAMATE HERBICIDES

[75] Inventors: Hermann Rempfler, Ettingen, Switzerland; Fredrik Cederbaum, Kobe, Japan; Felix Spindler, Starrkirch-Wil; Willy Urs Lottenbach, Aesch, both of Switzerland

[73] Assignee: Novartis Finance Corporation, New York, N.Y.

[21] Appl. No.: 09/128,651

[22] Filed: Aug. 4, 1998

Related U.S. Application Data

[62] Division of application No. 08/849,142, filed as application No. PCT/EP95/04612, Nov. 22, 1995, Pat. No. 5,831,114.

[30] Foreign Application Priority Data

Dec. 2, 1994 [CH] Switzerland .............. 3652/94

[51] Int. Cl.$^6$ .............. C07D 317/44; C07C 43/00
[52] U.S. Cl. .............. 549/437; 568/584; 568/588
[58] Field of Search .............. 549/437; 568/584, 568/588

[56] References Cited

U.S. PATENT DOCUMENTS

| | | |
|---|---|---|
| 4,016,186 | 4/1977 | Kondo et al. . |
| 4,722,935 | 2/1988 | Ehrenfreund . |
| 4,859,783 | 8/1989 | Ehrenfreund . |
| 5,078,783 | 1/1992 | Baker . |
| 5,099,059 | 3/1992 | Baker . |
| 5,152,827 | 10/1992 | Baker . |
| 5,194,661 | 3/1993 | Baker . |
| 5,393,885 | 2/1995 | Karrer . |

FOREIGN PATENT DOCUMENTS

| | | |
|---|---|---|
| 0 584 046 | 2/1994 | European Pat. Off. . |
| 94/10132 | 5/1994 | WIPO . |

OTHER PUBLICATIONS

J. Organoment. Chem. 415, p. 127 (1991).
J. Am. Chem. Soc. 110, pp. 629–631 (1988).
J. Am. Chem. Soc. 68, pp. 38–40 (1946), Hurd et al.
Houben–Weyl, "Methoden der Organishchen Chemie", Thieme–Verlag Stuttgart, 1952, vol. VIII, pp. 119–125.
Houben–Weyl, "Methoden der Organischen Chemie", Thieme–Verlag Stuttgart, 1957, vol. XI/1.

*Primary Examiner*—Deborah C. Lambkin
*Attorney, Agent, or Firm*—William A. Teoli, Jr.; John D. Peabody, III

[57] ABSTRACT

Substituted N-phenyl- and N-heteroarylalkylcarbamates of the formula I

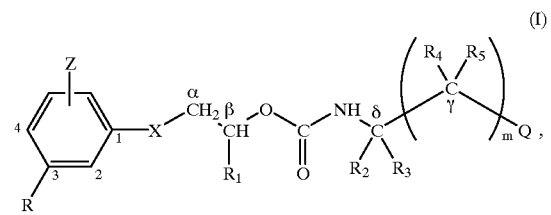

in which
Q is a group

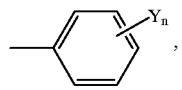

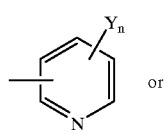

or

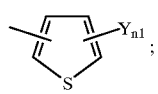

R is halogen, trifluoromethyl, cyano, nitro or $C_1$–$C_3$haloalkoxy;
Z is hydrogen or halogen; or
Z and R together in the 2- and 3-position of the phenyl ring form a group —$OCF_2O$—;
$R_1$ is $C_1$–$C_5$alkyl;
$R_2$, $R_3$, $R_4$ and $R_5$, independently of one another, are hydrogen, methyl or ethyl;
X is oxygen, sulfur, —SO— or —$SO_2$—;
Y is hydrogen, halogen, $C_1$–$C_3$alkyl, $C_1$–$C_3$haloalkyl, $C_1$–$C_3$alkoxy or cyano;
n is 0, 1 or 2;
$n_1$ is 0 or 1; and
m is 0 or 1,
with the proviso that m is 1 if Q is group (1) or (2);
and the diastereomers and enantiomers thereof,
exhibit pre- and post-emergence herbicidal properties. The preparation of these compounds and their use as herbicidally active ingredients are described.

3 Claims, No Drawings

CARBAMATE HERBICIDES

This appl is a div of Ser. No. 08/849,142 U.S. Pat. No. 5,831,144 which is a 371 of PCT EP95/04612 filed Nov. 22, 1995.

The present invention relates to novel, herbicidally active substituted N-phenyl- and N-heteroarylalkylcarbamates, to processes for their preparation, to compositions comprising these N-phenyl- and N-heteroarylalkylcarbamates as active ingredients, and to their use for controlling weeds, especially in crops of useful plants, for example cereals, rice, maize, soya beans and cotton.

Substituted alkyl- and phenylcarbamates which are herbicidally active have already been disclosed and are described, for example, in U.S. Pat. No. 5,078,783, U.S. Pat. No. 5,099,059, U.S. Pat. No. 5,152,827, U.S. Pat. No. 5,194,661 and U.S. Pat. No. 5,399,545.

There have now been found novel substituted N-phenyl- and N-heteroarylalkylcarbamates which have herbicidal properties and are distinguished by a good activity.

The compounds according to the invention are those of the formula I (I)

[Structural formula showing phenyl ring with Z, R substituents connected via X-CH₂-CH(R₁)-O-C(=O)-NH-C(R₂)(R₃)-[C(R₄)(R₅)]ₘ-Q]

in which
Q is a group (1) [phenyl ring with Yₙ substituent]

or (2) [pyridine ring with Yₙ substituent]

(3) [thiophene ring with Yₙ₁ substituent]

R is halogen, trifluoromethyl, cyano, nitro or C₁–C₃haloalkoxy;
Z is hydrogen or halogen; or
Z and R together in the 2- and 3-position of the phenyl ring form a group —OCF₂O—;
R₁ is C₁–C₅alkyl;
R₂, R₃, R₄ and R₅, independently of one another, are hydrogen, methyl or ethyl;
X is oxygen, sulfur, —SO— or —SO₂—;
Y is hydrogen, halogen, C₁–C₃alkyl, C₁–C₃haloalkyl, C₁–C₃alkoxy or cyano;
n is 0, 1 or 2;
n₁ is 0 or 1; and
m is 0 or 1,
with the proviso that m is 1 if Q is group (1) or (2);

and the diastereomers and enantiomers thereof.

In the above definitions, halogen is to be understood as meaning iodine, preferably fluorine, chlorine and bromine.

Suitable alkyl groups are straight-chain or branched alkyl groups, for example methyl, ethyl, n-propyl, isopropyl, n-butyl, sec-butyl, isobutyl, tert-butyl, n-pentyl and its isomers; preferably methyl and ethyl.

Suitable haloalkyl groups are mono- or polysubstituted alkyl groups, in particular alkyl groups which are mono- to trisubstituted by halogen, halogen specifically being understood to mean bromine or iodine and, in particular, fluorine or chlorine, for example fluoromethyl, difluoromethyl, chloromethyl, dichloromethyl, trichloromethyl and, in particular, trifluoromethyl.

Suitable alkoxy groups are, for example, methoxy, ethoxy, n-propyloxy and iso-propyloxy.

Suitable haloalkoxy groups are, for example, difluoromethoxy, trifluoromethoxy, 2,2,2-trifluoroethoxy, 1,1,2,2-tetrafluoroethoxy; preferably difluoromethoxy and trifluoromethoxy.

The N-phenyl- and N-heteroaryl-alkylcarbamates of the formula I according to the invention have a good selectivity in crops of useful plants, such as cereals, rice, maize, soya beans and cotton, when applied post-emergence, but in particular when applied pre-emergence.

The result of a possible existence of at least one asymmetric carbon atom in the compounds of the formula I in the β position relative to the phenyl-X group and on the benzyl γ- and/or δ-carbon atom if R₄ and R₂ differ from R₅ and R₃, respectively, is that the compounds can occur both as optically active isomers and in the form of racemic mixtures. The optically active compounds of the formula I can be obtained from the racemic mixtures by known separation methods, for example fractional crystallization, or by enantioselective synthesis. The active ingredients of the formula I in the present invention are to be understood as meaning all pure optical antipodes, but also the racemates. Unless specific mention is made to individual optical antipodes, the formula given is to be understood as indicating those racemic mixtures which result from the preparation process indicated.

Preferred compounds of the formula I are those in which the radical R is chlorine, bromine, trifluoromethyl or trifluoromethoxy.

Other preferred compounds of the formula I are those in which Z is hydrogen or fluorine.

Other preferred compounds of the formula I are those in which R₁ is methyl or ethyl.

Further preferred compounds of the formula I are those in which R₂, R₃, R₄ and R₅ independently of one another are hydrogen or methyl. Particularly preferred amongst these compounds are those in which R₂, R₃ and R₄ are hydrogen and R₅ is methyl.

Also preferred compounds of the formula I are those in which R₂, R₃ and R₄ are hydrogen, R₅ is methyl or ethyl and Q is group (1), (2) or (3). Particularly preferred amongst these compounds are those in which R₅ is methyl and Q is group (1) or (2).

Further preferred compounds of the formula I are those in which X is oxygen or sulfur.

Other preferred compounds of the formula I are those in which Q is group (1) or (2); n is 1; and Y is bonded in the ortho- or meta-position relative to the bonding site. Particularly preferred amongst these compounds are those in which Y is bonded in the ortho-position relative to the bonding site.

Furthermore preferred compounds of the formula I are those in which Y is hydrogen, fluorine, chlorine, methyl, trifluoromethyl, methoxy or cyano.

Important compounds of the formula I are those in which Q is group (1); R is chlorine, cyano, nitro, trifluoromethyl, trifluoromethoxy or difluoromethoxy; Z is hydrogen; or Z and R together in the 2- and 3-position of the phenyl ring form a group —OCF$_2$O—; X is oxygen or sulfur; Y is hydrogen, 2-fluoro, 2- or 3-chloro, 2-methyl or 2-trifluoromethyl; n is 0 or 1; R$_1$ is methyl or ethyl; R$_2$ is hydrogen; and R$_3$, R$_4$ and R$_5$ independently of one another are hydrogen or methyl.

Other important compounds of the formula I are those in which Q is the group

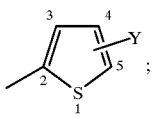

R is trifluoromethyl or trifluoromethoxy; Z is hydrogen; or Z and R together in the 2- and 3-position of the phenyl ring form a group —OCF$_2$O—; X is oxygen or sulfur; Y is hydrogen, 3- or 5-chloro or 3-methy; R$_1$ is ethyl; R$_2$ is hydrogen or methyl; R$_3$ is hydrogen; and m is 0.

Also important compounds of the formula I are those in which Q is the group

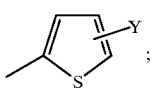

R is trifluoromethyl or trifluoromethoxy; Z is hydrogen; or Z and R together in the 2- and 3-position of the phenyl ring form a group —OCF$_2$O—; X is oxygen or sulfur; Y is hydrogen, 3-chloro or 3-methyl; R$_1$ is ethyl; R$_2$ and R$_3$ are hydrogen; R$_4$ and R$_5$ independently of one another are hydrogen or methyl; and m is 1.

Important compounds of the formula I are those in which Q is the group

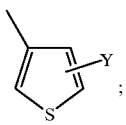

R is trifluoromethyl or trifluoromethoxy; Z is hydrogen; or Z and R together in the 2- and 3-position of the phenyl ring form a group —OCF$_2$O—; X is oxygen; Y is hydrogen; R$_1$ is ethyl; R2 is hydrogen or methyl; R$_3$ is hydrogen; and m is 0.

Other important compounds of the formula I are those in which Q is the group

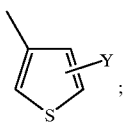

R is trifluoromethyl or trifluoromethoxy; Z is hydrogen; or Z and R together in the 2- and 3-position of the phenyl ring form a group —OCF$_2$O—; X is oxygen; Y is hydrogen; R$_1$ is ethyl; R$_2$ and R$_3$ are hydrogen; R$_4$ and R$_5$ independently of one another are hydrogen or methyl; and m is 1.

Also important compounds of the formula I are those in which Q is the group

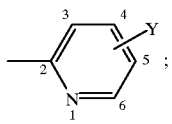

R is trifluoromethyl or trifluoromethoxy; Z is hydrogen; or Z and R together in the 2- and 3-position of the phenyl ring form a group —OCF$_2$O—; X is oxygen; Y is hydrogen or 3-methyl; R$_1$ is ethyl; R$_2$, R$_3$ and R$_5$ are hydrogen; R$_4$ is hydrogen or methyl; and m is 1.

Particularly preferred compounds to be mentioned are those of the formula Ia and Ib

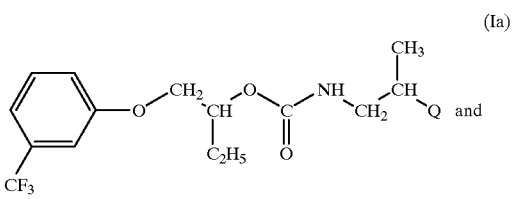

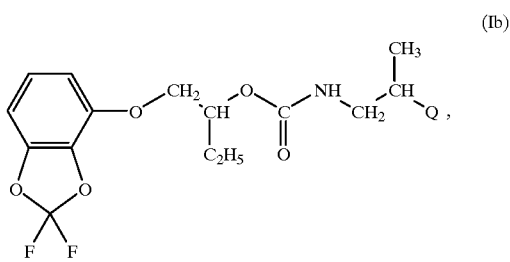

in which Q is as defined for formula I Amongst these, very particularly important are those compounds of the formula Ia and Ib in which Q is the group

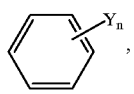

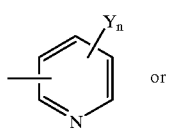

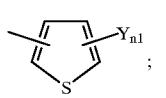

Y is hydrogen, fluorine, chlorine, methyl, trifluoromethyl, methoxy or cyano; n is 0, 1 or 2; and n$_1$ is 0 or 1.

Also preferred compounds of the formula I are those in which the β-carbon atom is present in optically pure form as the (−)-enantiomer.

The process according to the invention for the preparation of the compounds of the formula I is carried out analogously to known processes and comprises, a) to prepare the compounds of the formula I, reacting a compound of the formula II

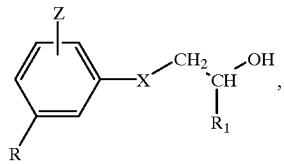
(II)

in which R, Z, $R_1$ and X are as defined for formula I with a benzyl isocyanate of the formula III

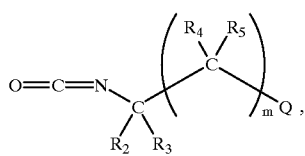
(III)

in which $R_2$, $R_3$, $R_4$, $R_5$, Q and m are as defined for formula I in an inert organic solvent in the presence or absence of a catalyst; or b) first chloroformylating a compound of the formula II

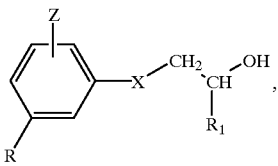
(II)

under customary conditions, preferably using phosgene or diphosgene, to give a compound of the formula IV

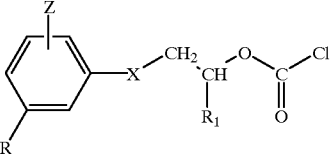
(IV)

where, in formulae II and IV the radicals R, Z, $R_1$ and X are as defined for formula I, and subsequently reacting this product with an amine of the formula V

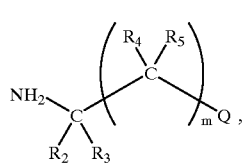
(V)

in which $R_2$, $R_3$, $R_4$, $R_5$, Q and m are as defined for formula I in an inert organic solvent in the presence of a proton scavenger, for example tertiary amines or pyridine. Process variants a) and b) follow equation 1.

Equation 1:

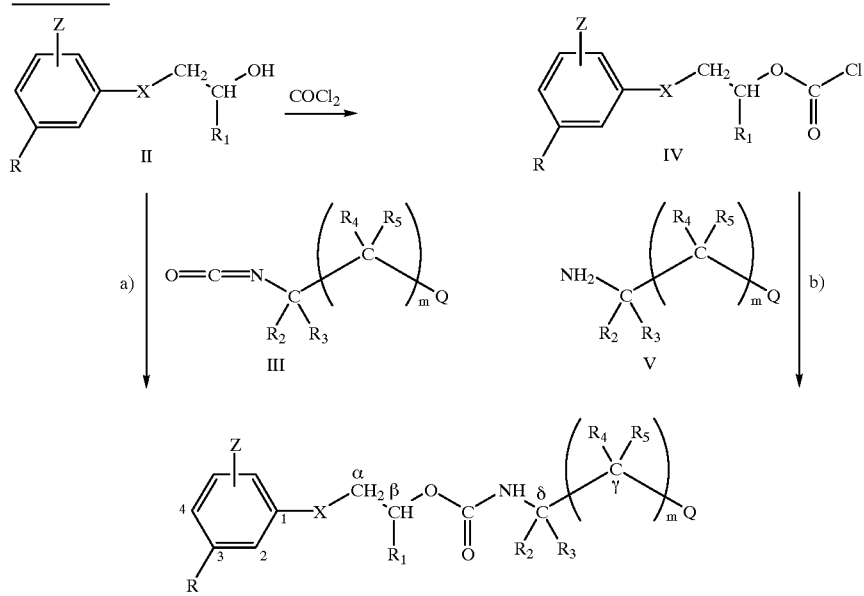

The addition reaction in accordance with process variant a) can expediently be carried out by reacting the alcohol of the formula II and the isocyanate of the formula III in an inert aprotic organic solvent, such as an aliphatic or cyclic ether, for example diethyl ether, 1,2-dimethoxyethane, tetrahydrofuran or dioxane, or a chlorinated aliphatic hydrocarbon, for example methylene chloride, or an aromatic, for example toluene or xylene, or an aliphatic ester, for example ethyl acetate, in the presence of a catalyst, for example 4-N,N-dimethylaminopyridine, triethylamine, dibutyltin dilaurate and/or dibutyltin diacetate, preferably at temperatures of between 20° C. and the reflux temperature of the reaction solution.

In process variant b), the chloroformate of the formula IV and the amine of the formula V are expediently reacted in an inert aprotic organic solvent in the presence of an organic base, analogously to the procedure described in process variant a), at temperatures of between −20° C. and +40° C., preferably between +5° C. and +20° C. For working-up, the resulting reaction mixture is washed, preferably using water and dilute acid, to remove amine by-products in the form of salts.

The alcohols of the formula II (IIa: $X_1$=—O— or —S—; IIb; and IIc) can be prepared by known standard methods (for example U.S. Pat. No. 5,099,059 and WO 94/10 132), for example as described in equation 2 below.

Equation 2

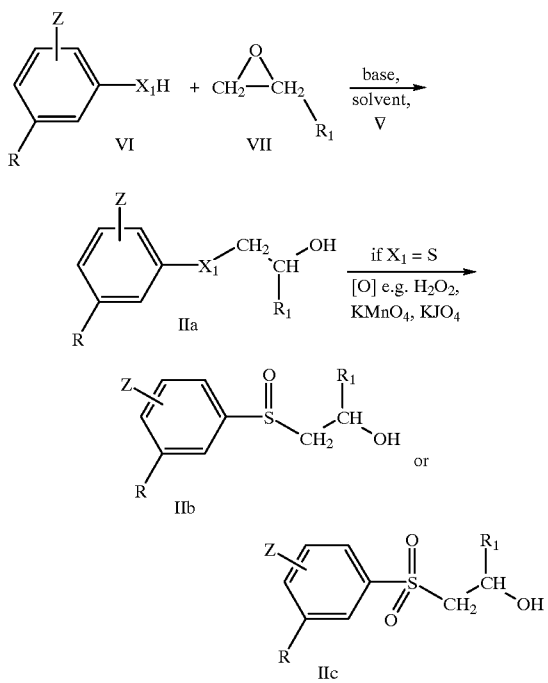

The intermediates of the formula IIa can also be prepared under pressure in the presence of lithium hydroxide monohydrate and in the absence of solvents, as described in WO 94/10132.

The alcohols of the formula II can be separated to give the enantiomers for example with the aid of liquid chromatography on chiral carriers, for example HPLC on Chiracel—OD—H (Daicel) and 2% isopropanol in n-hexane as the eluent.

A further possibility of obtaining enantiomerically pure alcohols of the formula II is the enantioselective hydrogenation of α-phenoxyketones using BINAP/Ru(II) catalyst complexes.

The (−) enantiomer of the compounds of the formula II is to be understood as the optical antipode of the formula IIe which is first, i.e. before the (+) enantiomer, eluted by means of HPLC on a Chiracel—OD—H column by Daicel using the mixture of n-hexane and 2% of isopropanol as the eluent, or which is formed predominantly (enantiomeric excess up to >96%) in the enantioselective hydrogenation of α-phenoxyketones using $Ru_2Cl_4[(R)\text{-BINAP}]_2[N(C2H_5)_3]$ catalyst complex (equation 2a).

The process according to the invention for the preparation of optically active compounds of the formula IIe

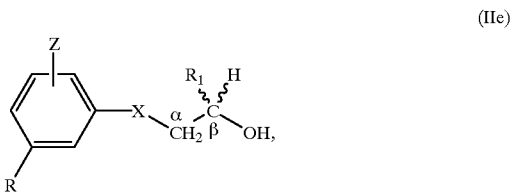

in which R, $R_1$, X and Z are as defined in claim 1 and the β-carbon atom is present in optically pure form as the (−) enantiomer comprises subjecting the compound of the formula VIII

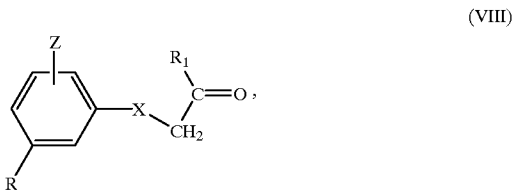

in which R, $R_1$, X and Z are as defined above to a (R)-BINAP/Ru(II)-catalysed hydrogenation reaction in an alcoholic solvent, for example methanol or ethanol, in the presence or absence of a catalytic amount of a protonic acid, for example hydrochloric acid or nitric acid.

The process in which α-phenoxy ketones of the formula VIII are subjected to enantioselective hydrogenation using (R)-BINAP/Ru(II) catalysts is as shown in equation 2a.

Equation 2a:

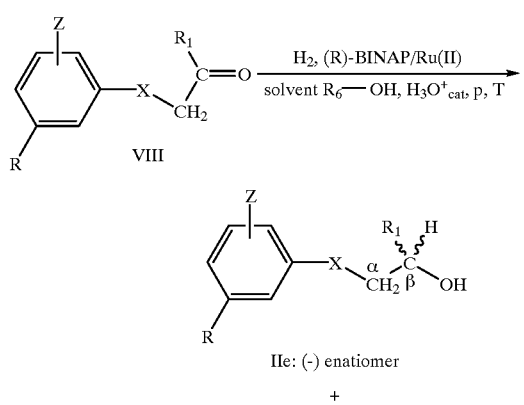

IIe: (−) enatiomer

+

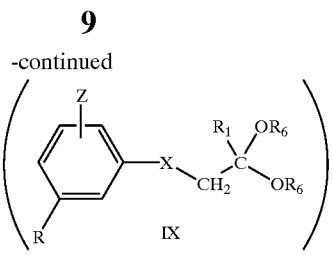

Enantioselective homogeneous hydrogenation reactions of α-functionalized ketones with BINAP-Ru(II) catalyst complexes are known and described, for example, in J. Am. Chem. Soc. 110, 629 (1988).

The enantioselective hydrogenation reaction according to the invention starts from the ketones of the formula VIII and is novel.

The ketones of the formula VIII are either known or can be prepared readily by known processes, for example as described in J. Am. Chem. Soc. 68, 38 (1946).

The enantioselective hydrogenation reaction is expediently carried out in alcohols, for example $R_6$—OH, in which $R_6$ is $C_1$–$C_4$alkyl, in particular in methanol and ethanol. The catalysts employed are BINAP/Ru(II) complexes, for example as described in U.S. Pat. No. 4,691,037, but in particular $Ru_2Cl_4[(R)-2,2'-bis(diphenylphosphino)-1,1'-dinaphthyl]_2[N(C_2H_5)_3]=Ru_2Cl_4[(R)-BINAP]_2[N(C_2H_5)_3]$. The concentration of the catalyst complex is not critical for the course of the enantioselective hydrogenation. If desired, a protonic acid, for example hydrochloric or nitric acid, can be added to act as co-catalyst. The hydrogenation is preferably carried out at pressures from atmospheric pressure to 100 bar, in particular under slightly elevated pressure up to 80 bar, and at temperatures of from 10° C. to the boiling point of the solvent used, preferably at temperatures of from 20° C. to 40° C.

Under standard hydrogenation conditions in dilute alcoholic solutions $R_6$—OH, in which $R_6$ is $C_1$–$C_4$alkyl, for example the 1.0 to 1.2-molar concentration of the ketone of the formula VIII, the acetal of the formula IX is formed in variable amounts, up to 30%, as an undesirable, stable by-product. This acetal is also formed in hydrogenation reactions without added acid.

The abovementioned formation of acetals on certain metal complexes, in particular on Ru(II) complexes, is examined, for example, in J. Organomet. Chem. 415, 127 (1991) and Synlett 1993, 751.

According to J. Am. Chem. Soc. 117,4423 (1995), the acetal formation in the course of the enantioselective hydrogenation of β-keto esters in the presence of i-Pr-BPE/Ru(II) as the catalyst can be suppressed by adding water (10% mixture of water and methanol).

Surprisingly, it is now found that the acetal formation can be suppressed largely or even completely when the concentration of the ketone of the formula VIII in the hydrogenation solution is increased; for example, only a maximum of 20% of acetal of the formula IX are formed in an approximately 30% hydrogenation solution (approximately 1.3-molar concentration of ketone of the formula VIII), and no more acetal of the formula IX at all in an approximately 65% hydrogenation solution (approximately 2.8-molar concentration of ketone of the formula VIII).

The yield of crude alcohol of the formula II is generally >90%, the enantiomeric excess of desirable (−) enantiomer IIe being up to >96% under the reaction conditions indicated, depending on the substituents R, $R_1$, X and Z. The absolute configuration (not known in the present case) of the alcohol formed is determined by the configuration of the catalyst complex used. In the enantioselective hydrogenation process according to the invention, the use of $Ru_2Cl_4$ [(R)-BINAP]$_2$[N(C$_2$H$_5$)$_3$] complex mainly leads to the desirable (−) enantiomeric alcohol of the formula IIe.

The optically pure alcohols of the formula IIe((−) enantiomers) are novel and therefore also provided by the present invention.

The enantioselective synthesis of the compounds of the formula I which are optically active in the β-position relative to the phenyl-X group ((−) enantiomers) from the corresponding optically active alcohols of the formula IIe ((−) enantiomers) can be effected for example by a method similar to process variants a) and b) described (equation 1).

The isocyanates of the formula III are either commercially available or can be prepared analogously to known processes, for example as described in Houben-Weyl, "Methoden der Organischen Chemie" [Methods in Organic Chemistry], Vol. VIII, page 119 et seq., Thieme-Verlag Stuttgart, 1952.

The amines of the formula V are either commercially available or can be prepared analogously to known processes, for example as described in Houben-Weyl, "Methoden der Organischen Chemie" [Methods in Organic Chemistry], Vol. XI(1), Thieme-Verlag Stuttgart, 1957.

The chloroformate derivatives of the formula IV are synthesized by methods known per se, for example as described in U.S. Pat. No. 5,099,059, U.S. Pat. No. 5,078,783 and WO 94/10132.

The compounds of the formulae I, IIa, IIb, IIc and IV can be isolated and purified by methods known per se. Those skilled in the art will also be aware of the sequence in which certain reactions are expediently to be carried out under process variants a) and b) to avoid potential secondary reactions.

Unless a targeted synthesis for isolating pure isomers is carried out, the product can be obtained in the form of a mixture of two or more isomers. The isomers can be separated by methods known per se.

The intermediates of the formula IId

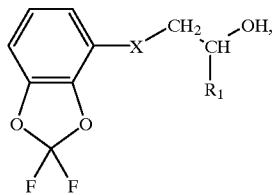

(IId)

in which $R_1$ and X are as defined in formula I are disclosed in WO 94/10132.

The same preferences given for the compounds of the formula I apply to the intermediates of the formulae II and IV.

The starting compounds of the formulae VI and VII required for the preparation processes are either known or can be prepared by various processes known from the literature, for example as described in equation 3 below in the case of compounds of the formula VIa.

Equation 3:

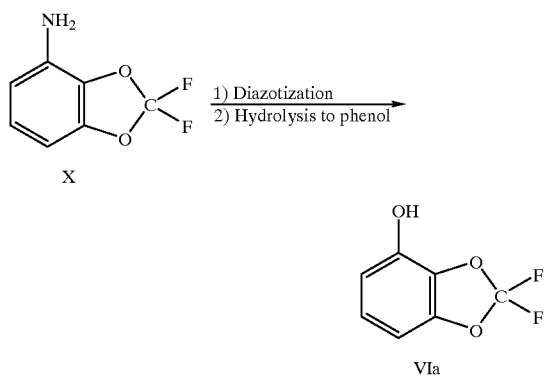

The preparation of the starting compound required, of the formula X, is described in EP-A-0 198 797.

The formulations, i.e. the compositions, preparations or products comprising the active ingredient of the formula I in the presence or absence of one or more solid or liquid additives, are prepared in a known manner, for example by intimately mixing and/or grinding the active ingredients with extenders, for example solvents, solid carriers and, if desired, surface-active compounds (surfactants).

Suitable solvents may be: aromatic hydrocarbons, in particular the fractions $C_8$ to $C_{12}$, such as mixtures of alkylbenzenes, for example xylene mixtures, or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether, ketones such as cyclohexanone, isophorone or diacetone alcohol, strongly polar solvents, such as N-methyl-2-pyrrolidone, dimethyl sulfoxide or water, vegetable oils and their esters, such as rapeseed oil, castor oil or soya oil; if desired also silicone oils.

Solid carriers, for example for dusts and dispersible powders, which are generally used are ground natural minerals, such as calcite, talc, kaolin, montmorillonite or attapulgite. To improve the physical properties, it is also possible to add highly-disperse silica or highly-disperse absorptive polymers. Suitable particulate, adsorptive carriers for granules are porous types, for example pumice, brick grit, sepiolite or bentonite, unsuitable non-sorptive carrier materials are, for example, calcite or sand. In addition, a large number of pregranulated materials of inorganic or organic nature, such as, in particular, dolomite or comminuted plant residues.

Suitable surface-active compounds are, depending on the nature of the active ingredient of the formula I to be formulated, non-ionic, cationic and/or anionic surfactants which have good emulsifying, dispersing and wetting properties. Surfactants are all understood as meaning surfactant mixtures.

Suitable anionic surfactants can be either water-soluble soaps or water-soluble synthetic surface-active compounds.

Soaps which are suitable are the alkali metal salts, alkaline earth metal salts or substituted or unsubstituted ammonium salts of higher fatty acids ($C_{10}$–$C_{22}$) for example the sodium salts or potassium salts of oleic or stearic acid, or of natural fatty acid mixtures which can be obtained from, for example, coconut oil or tallow oil. Other surfactants which may be mentioned are the fatty acid methyltaurinates.

However, so-called synthetic surfactants are used more frequently, in particular fatty alcohol sulfonates, fatty alcohol sulfates, sulfonated benzimidazole derivatives or alkylarylsulfonates.

The fatty alcohol sulfonates or fatty alcohol sulfates are, as a rule, in the form of the alkali metal salts, alkaline earth metal salts or substituted or unsubstituted ammonium salts and have an alkyl radical having 8 to 22 carbon atoms, alkyl also including the alkyl moiety of acyl radicals, for example the sodium or calcium salt of lignosulfonic acid, of the dodecyl sulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives comprise preferably 2 sulfonyl groups and a fatty acid radical having 8–22 carbon atoms. Examples of alkylaryl sulfonates are the sodium, calcium or triethanolamine salts of dodecylbenzenesulfonic acid, of dibutylnaphthalenesulfonic acid or of a naphthalenesulfonic acid/formaldehyde condensation product.

Suitable phosphates, for example salts of the phosphoric ester of a p-nonylphenol/(4–14)ethylene oxide adduct, or phospholipids, are also suitable.

Suitable nonionic surfactants are mainly polyglycol ether derivatives of aliphatic or cycloaliphatic alcohols, saturated or unsaturated fatty acids and alkylphenols, which can comprise 3 to 30 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble polyethylene oxide adducts with polypropylene glycol, ethylene diaminopolypropylene glycol and alkylpolypropylene glycol which have 1 to 10 carbon atoms in the alkyl chain and comprise 20 to 250 ethylene glycol ether groups and 10 to 100 propylene glycol ether groups. The abovementioned compounds conventionally comprise 1 to 5 ethylene glycol units per propylene glycol unit.

Examples of nonionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Other substances which are suitable are fatty acid esters of polyoxyethylene sorbitan, such as polyoxyethylene sorbitan trioleate.

The cationic surfactants are mainly quaternary ammonium salts which comprise, as N substituents, at least one alkyl radical having 8 to 22 carbon atoms and as further substituents lower, halogenated or unhalogenated alkyl, benzyl or lower hydroxyalkyl radicals. The salts are preferably in the form of halides, methylsulfates or ethylsulfates, for example stearyltrimethylammonium chloride or benzyldi(2-chloroethyl)ethylammonium bromide.

The surfactants conventionally used in the art of formulation are described, inter alia, in the following publications:
"McCutcheon's Detergents and Emulsifiers Annual", Mc Publishing Corp., Glen Rock, N.J., 1988.
M. and J. Ash, "Encyclopedia of Surfactants", Vol. I-III, Chemical Publishing Co., New York, 1980–1981.
Dr. Helmut Stache "Tensid-Taschenbuch" [Surfactants Guide], Carl Hanser Verlag, Munich/Vienna 1981.

As a rule, the herbicidal preparations comprise 0.1 to 99%, in particular 0.1 to 95%, of active ingredient of the formula I, 1 to 99% of a solid or liquid additive and 0 to 25%, in particular 0.1 to 25%, of a surfactant.

While concentrated compositions are more preferred as commercially available goods, the end consumer uses, as a rule, dilute compositions.

The compositions can also comprise other additives such as stabilizers, for example epoxidized or unepoxidized vegetable oils (epoxidized coconut oil, rapeseed oil or soya oil), antifoam, for example silicone oil, preservatives, viscosity regulators, binders, tackifiers and fertilizers or other active ingredients for achieving specific effects.

In particular, preferred formulations are composed as follows: (%=per cent by weight)

Emulsifiable concentrates:

| | |
|---|---|
| Active ingredient: | 1 to 90%, preferably 5 to 50% |
| Surfactant: | 5 to 30%, preferably 10 to 20% |
| Liquid carrier: | 15 to 94%, preferably 70 to 85% |

Dusts:

| | |
|---|---|
| Active ingredient: | 0.1 to 10%, preferably 0.1 to 1% |
| Solid carrier: | 99.9% to 90%, preferably 99.9 to 99% |

Suspension concentrates:

| | |
|---|---|
| Active ingredient: | 5 to 75%, preferably 10 to 50% |
| Water: | 94 to 24%, preferably 88 to 30% |
| Surfactant: | 1 to 40%, preferably 2 to 30% |

Wettable powders:

| | |
|---|---|
| Active ingredient: | 0.5 to 90%, preferably 1 to 80% |
| Surfactant: | 0.5 to 20%, preferably 1 to 15% |
| Solid carrier: | 5 to 95%, preferably 15 to 90% |

Granules:

| | |
|---|---|
| Active ingredient: | 0.5 to 30%, preferably 3 to 15% |
| Solid carrier: | 99.5 to 70%, preferably 97 to 85% |

A. Formulation examples for active ingredients of the formula I
(% = percent by weight)

| 1. Wettable powders | a) | b) | c) |
|---|---|---|---|
| Active ingredient of Tables 1–6 | 20% | 50% | 0.5% |
| Sodium lignosulfonate | 5% | 5% | 5% |
| Sodium lauryl sulfate | 3% | — | — |
| Sodium diisobutylnaphthalene-sulfonate | — | 6% | 6% |
| Octylphenol polyethylene glycol ether (7–8 mol of EO) | — | 2% | 2% |
| Highly-disperse silica | 5% | 27% | 27% |
| Kaolin | 67% | — | — |
| Sodium chloride | — | — | 59.5% |

The active ingredient is mixed intimately with the additives and the mixture is ground thoroughly in a suitable mill. This gives wettable powders which can be diluted with water to suspensions of any desired concentration.

| 2. Emulsion concentrates | a) | b) |
|---|---|---|
| Active ingredient of Tables 1–6 | 10% | 1% |
| Calcium dodecylbenzenesulfonate | 3% | 3% |
| Octylphenol polyethylene glycol ether (4–5 mol of EO) | 3% | 3% |
| Castor oil polyethylene glycol ether (36 mol of EO) | 4% | 4% |
| Cyclohexanone | 30% | 10% |
| Xylene mixture | 50% | 79% |

Emulsions of any desired concentration can be prepared from such concentrates by diluting them with water.

| 3. Dusts | a) | b) |
|---|---|---|
| Active ingredient of Tables 1–6 | 0.1% | 1% |
| Talc | 99.9% | — |
| Kaolin | — | 99% |

Ready-to-use dusts are obtained by intimately mixing the carriers with the active ingredient.

| 4. Extruder granules | a) | b) |
|---|---|---|
| Active ingredient of Tables 1–6 | 10% | 1% |
| Sodium lignosulfonate | 2% | 2% |
| Carboxymethylcellulose | 1% | 1% |
| Kaolin | 87% | 96% |

The active ingredient is mixed with the additives, and the mixture is ground and moistened with water. This mixture is extruded and subsequently dried in a stream of air.

| 5. Coated granules | |
|---|---|
| Active ingredient of Tables 1–6 | 3% |
| Polyethylene glycol (MW200) | 3% |
| Kaolin | 94% |

In a mixer, the kaolin which has been moistened with polyethylene glycol is coated uniformly with the finely ground active ingredient. This gives dust-free coated granules.

| 6. Suspension concentrate | a) | b) |
|---|---|---|
| Active ingredient of Tables 1–6 | 5% | 40% |
| Ethylene glycol | 10% | 10% |
| Nonylphenol polyethylene glycol ether (15 mol of EO) | 1% | 6% |
| Sodium lignosulfonate | 5% | 10% |
| Carboxymethylcellulose | 1% | 1% |
| 37% aqueous formaldehyde solution | 0.2% | 0.2% |
| Silicone oil in the form of a 75% aqueous emulsion | 0.8% | 0.8% |
| Water | 77% | 32% |

The finely ground active ingredient is mixed intimately with the additives. This gives a suspension concentrate from which suspensions of any desired concentration can be prepared by diluting it with water.

| 7. Salt solution | |
|---|---|
| Active ingredient of Tables 1–6 | 5% |
| Isopropylamine | 1% |
| Octylphenol polyethylene glycol ether (78 mol of EO) | 91% |

The compounds of the formula I are employed in unaltered form, as they can be obtained from synthesis, or, preferably, as compositions together with the auxiliaries conventionally used in the art of formulation, and they are therefore processed in a known manner to give, for example, emulsion concentrates, ready-to-spray or ready-to-dilute solutions, dilute emulsions, wettable powders, soluble powders, dusts, granules, and also encapsulations, for example in polymeric substances. The methods of application, such as spraying, atomizing, dusting, spreading or pouring, and the nature of the compositions are selected to suit the intended aims and the prevailing circumstances. As a rule, the rates of application are 0.005 to 2 kg per hectare, preferably 0.01 to 1 kg per hectare.

B. PREPARATION EXAMPLES

Example H1

1-(3-Trifluoromethylphenoxy)-2-butanol (intermediate)

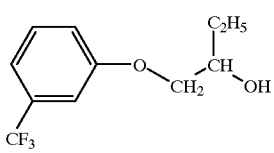

In a bomb tube (pressurized vessel), 40.5 g of 3-hydroxybenzotrifluoride, 18.0 g of α-butylene oxide and 1.0 g of lithium hydroxide monohydrate are heated for 16 hours at 140° C. After the reaction vessel has cooled, the reaction mixture is dissolved in 200 ml of ethyl acetate, and the organic phase is washed with water and subsequently dried over sodium sulfate. After concentration, the desired product 1-(3-trifluoromethylphenoxy)-2-butanol is obtained in a yield of 54.0 g and in high purity. The product can be employed in the subsequent reaction without further purification.

Example H2

1-(3-Chlorophenoxy)-2-butanol (intermediate) is obtained analogously to Example HI by using 51.4 g of 3-chlorophenol, 28.8 g of α-butylene oxide and 1.0 g of lithium hydroxide monohydrate in a yield of 71.4 g in the form of an oil; b.p. 83–84° C./0.04 torr.

Example H3

1-(3-Cyanophenoxy)-2-butanol (intermediate) is obtained analogously to Example HI by using 20.7 g of 3-cyanophenol, 13.8 g of α-butylene oxide and 0.5 g of lithium hydroxide monohydrate in a yield of 25.9 g in the form of an oil; b.p. 116–118° C./0.04 torr.

Example H4

O—(3-Trifluoromethylphenoxy)-2-butyl chloroformate (intermediate)

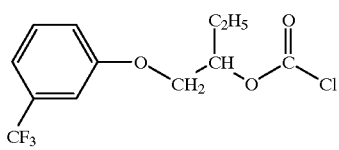

46.8 g of 1-(3-trifluoromethylphenoxy)butan-2-ol in 200 ml of toluene is added to 125 ml of a 1.93-molar solution of phosgene in toluene and 0.5 ml of N,N-dimethylformamide. After the slightly exothermic reaction has subsided, the mixture is heated for 8 hours at 60° C. After the reaction mixture has been concentrated, the desired product O—(3-trifluoromethylphenoxy)-2-butyl chloroformate is obtained in quantitative yield and can be employed in subsequent reaction without further purification.

Example H5

O—[1-(3-Trifluoromethylphenoxy)-2-butyl]-N-(2-phenylethyl) carbamate (Comp. No. 1.1)

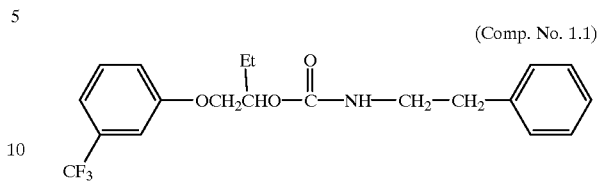

A solution of 1.2 g (0.01 mol) of 2-phenylethylamine and 1.1 g (0.011 mol) of triethylamine in 20 ml of methylene chloride is added dropwise to 2.9 g (0.01 mol) of O—(3-trifluoromethylphenoxy)-2-butyl chloroformate in 20 ml of methylene chloride. After 14 hours, the solution is poured into cold, dilute hydrochloric acid, and the organic phase is separated off, washed with water, dried using sodium sulfate and evaporated on a rotary evaporator. It is purified by means of column chromatography on silica gel using ethyl acetate/hexane ⅓ as the eluent, resulting in 3.4 g (80.5% of theory) of a colourless oil of refractive index $n_D^{25}$ 1.5015. The biologically active (–) isomer (the two (+) and (–) isomers are separated by chromatography at the level of the alcohol of the formula II) has the boiling point 49–50° C.

Example H6

(–) Enantiomer of 1-(3-trifluoromethylphenoxy)butan-2-ol (intermediate)

(Comp. No. 7.2)

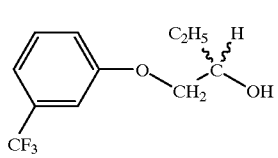

Using a steel capillary, 87.9 g of 1-(3-trifluoromethylphenoxy)butan-2-on, dissolved in 130 ml of methanol and 0.641 g of $Ru_2Cl_4[(R)-2,2'$-bis (diphenylphosphino)-1,1'-dinaphthyl$]_2[N(C_2H_5)_3]$=$Ru_2Cl_4$ $[(R)$-BINAP$]_2[N(C_2H_5)_3]$ and 1.2 ml of IN hydrochloric acid are transferred in succession into a steel autoclave under an argon atmosphere. In 3 cycles (20 bar, atmospheric pressure), the argon inert gas is displaced by hydrogen, and the mixture is subsequently hydrogenated at 20° C. under a hydrogen pressure of 80 bar. After 69 hours, the hydrogen uptake has ended. The reaction mixture is removed from the steel autoclave and evaporated on a rotary evaporator. The residue obtained is dissolved in ethyl acetate/n-hexane ¼ and filtered through a short silica gel column to remove the catalyst. After the collected fractions have been evaporated, the desired product is obtained in a yield of 87.9 g (99% of theory); refractive index $n_D^{22}$ 1.4611;

$[\alpha]_{365}^{20}$=–18.7±0.2˚ ($c$=1.0 in methanol).

The purity of the (–) enantiomer is measured by means of HPLC using a Chiracel—OD—H column (4.6×250 mm) by Daicel and using the mixture of n-hexane and 2% of isopropanol as the eluent.

The enantiomeric excess (ee) is 94.2% ((–) enantiomer).

Under the HPLC chromatography conditions given above, the (–) enantiomer is eluted first, i.e. before the (+) enantiomer.

The compounds of the formula I listed in Tables 1–6 below are prepared analogously.

The (−) enantiomers listed in Tables 1 and 2 below refer to the asymmetric carbon atom in the β-position relative to the phenyl-X group in the compounds of the formula I and are prepared from the corresponding (−) enantiomeric alcohols of the formula IIe.

TABLE 1

Compounds of the formula Ic

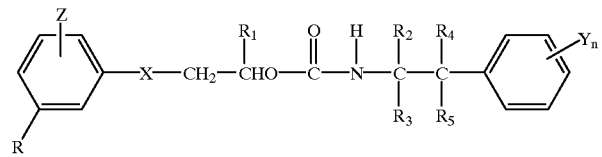

(Ic)

| Comp. No. | R | Z | X | n | Y | $R_1$ | $R_2$ | $R_3$ | $R_4$ | $R_5$ | Physical data |
|---|---|---|---|---|---|---|---|---|---|---|---|
| 1.1 | $CF_3$ | H | O |  | H | Et | H | H | H | H | $n_D^{25}$ 1.5015 |
| 1.2 | $CF_3$ | H | O | 1 | 2-Cl | Et | H | H | H | H | $n_D^{25}$ 1.5084 |
| 1.3 | $CF_3$ | H | O |  | H | Me | H | H | H | H |  |
| 1.4 | $CF_3$ | H | O | 1 | 2-Me | Et | H | H | H | H | $n_D^{25}$ 1.5067 |
| 1.5 | $CF_3$ | H | O |  | H | Et | H | H | Me | H | $n_D^{25}$ 1.5025 |
| 1.6 | $CF_3$ | H | O |  | H | Et | H | Me | H | H | m.p. 48–58° C. |
| 1.7 | $CF_3$ | H | S |  | H | Et | H | H | H | H |  |
| 1.8 | $CF_3$ | H | O | 1 | 2-$CF_3$ | Et | H | H | H | H |  |
| 1.9 | $CF_3$ | H | O | 1 | 3-Cl | Et | H | H | H | H |  |
| 1.10 | $CF_3$ | H | O | 1 | 4-F | Et | H | H | H | H |  |
| 1.11 | $CF_3$ | H | O |  | H | Et | H | H | Et | H |  |
| 1.12 | $CF_3$ | H | O |  | H | Et | H | Me | Me | H |  |
| 1.13 | $CF_3$ | H | O |  | H | Et | H | H | Me | Me |  |
| 1.14 | $OCF_3$ | H | O |  | H | Et | H | H | H | H |  |
| 1.15 | $OCF_3$ | H | O | 1 | 2-F | Et | H | H | H | H |  |
| 1.16 | $OCF_3$ | H | O | 1 | 2-Me | Et | H | H | H | H |  |
| 1.17 | $OCF_3$ | H | O | 1 | 2-Me | Et | H | H | Me | H |  |
| 1.18 | CN | H | O |  | H | Et | H | H | H | H |  |
| 1.19 | $NO_2$ | H | O |  | H | Et | H | H | H | H |  |
| 1.20 | Cl | H | O |  | H | Et | H | H | H | H |  |
| 1.21 | —O—$CF_2$—O— | | O |  | H | Et | H | H | H | H |  |
| 1.22 | —O—$CF_2$—O— | | O | 1 | 2-Me | Et | H | H | H | H |  |
| 1.23 | $CF_3$ | H | O | 1 | 2-Cl | Et | H | H | Me | H | $n_D^{25}$ 1.5113 |
| 1.24 | $CF_3$ | H | O | 1 | 2-Cl | Et | H | H | Me | Me | $n_D^{25}$ 1.5135 |
| 1.25 | $OCHF_2$ | H | O |  | H | Et | H | H | H | H |  |
| 1.26 | $CF_3$ | H | O |  | H | Et | H | H | H | H | m.p. 49–50° C.; (−) enantiomer |
| 1.27 | $CF_3$ | H | O |  | H | Et | H | H | Me | H | oil; (−) enantiomer |

TABLE 2

Compounds of the formula Id

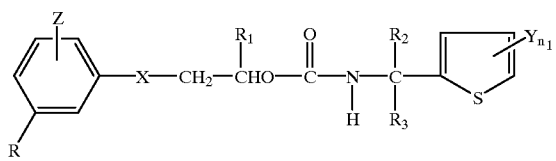

(Id)

| Comp. No. | R | Z | X | $n_1$ | Y | $R_1$ | $R_2$ | $R_3$ | Physical data |
|---|---|---|---|---|---|---|---|---|---|
| 2.1 | $CF_3$ | H | O |  | H | Et | H | H | $n_D^{25}$ 1.4989 |
| 2.2 | $CF_3$ | H | O |  | H | Et | Me | H |  |
| 2.3 | $CF_3$ | H | S |  | H | Et | H | H |  |
| 2.4 | $OCF_3$ | H | O |  | H | Et | H | H |  |
| 2.5 | $CF_3$ | H | O | 1 | 5-Cl | Et | H | H | 45–48° C. |
| 2.6 | $CF_3$ | H | O | 1 | 3-Me | Et | H | H | 60–62° C. |
| 2.7 | $CF_3$ | H | O | 1 | 3-Cl | Et | H | H | 68–70° C. |
| 2.8 | —O—$CF_2$—O— | | O |  | H | Et | H | H |  |
| 2.9 | $OCF_3$ | H | O | 1 | 3-Me | Et | H | H | 68° C.; (−) enantiomer |
| 2.10 | $OCF_3$ | H | O | 1 | 3-Cl | Et | H | H |  |

TABLE 2-continued

Compounds of the formula Id

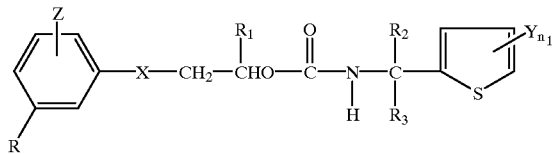

(Id)

| Comp. No. | R | Z | X | $n_1$ | Y | $R_1$ | $R_2$ | $R_3$ | Physical data |
|---|---|---|---|---|---|---|---|---|---|
| 2.11 | $CF_3$ | H | O | | H | Et | H | H | 65–66° C.; (−) enantiomer |
| 2.12 | $CF_3$ | H | O | 1 | 3-Me | Et | H | H | 77–78° C.; (−) enantiomer |

TABLE 3

Compounds of the formula Ie

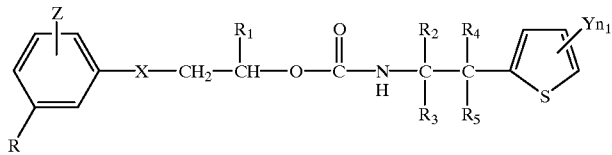

(Ie)

| Comp. No. | R | Z | X | $n_1$ | Y | $R_1$ | $R_2$ | $R_3$ | $R_4$ | $R_5$ | Physical data |
|---|---|---|---|---|---|---|---|---|---|---|---|
| 3.1 | $CF_3$ | H | O | | H | Et | H | H | H | H | oil |
| 3.2 | $CF_3$ | H | O | 1 | 3-Me | Et | H | H | H | H | oil |
| 3.3 | $CF_3$ | H | O | 1 | 3-Cl | Et | H | H | H | H | |
| 3.4 | $CF_3$ | H | O | | H | Et | H | H | Me | H | oil |
| 3.5 | $CF_3$ | H | O | 1 | 3-Me | Et | H | H | Me | H | |
| 3.6 | $CF_3$ | H | O | 1 | 3-Cl | Et | H | H | Me | H | |
| 3.7 | $CF_3$ | H | O | | H | Et | H | H | Me | Me | |
| 3.8 | —O—$CF_2$—O— | | O | | H | Et | H | H | H | H | |
| 3.9 | $CF_3$ | H | S | | H | Et | H | H | H | H | |
| 3.10 | $OCF_3$ | H | O | | H | Et | H | H | H | H | |
| 3.11 | $OCF_3$ | H | O | | H | Et | H | H | Me | H | |
| 3.12 | $OCF_3$ | H | O | 1 | 3-Me | Et | H | H | H | H | |
| 3.13 | $OCF_3$ | H | O | 1 | 3-Me | Et | H | H | Me | H | |

TABLE 4

Compounds of the formula If

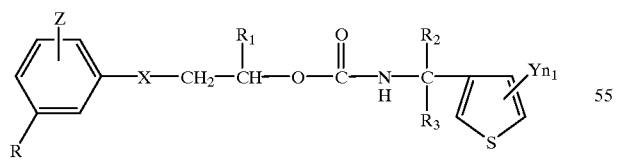

(If)

| Comp. No. | R | Z | X | $n_1$ | Y | $R_1$ | $R_2$ | $R_3$ | Physical data |
|---|---|---|---|---|---|---|---|---|---|
| 4.1 | $CF_3$ | H | O | | H | Et | H | H | 63–65° C. |
| 4.2 | $CF_3$ | H | O | | H | Et | Me | H | |
| 4.3 | $OCF_3$ | H | O | | H | Et | H | H | |

TABLE 5

Compounds of the formula Ig $$\text{(Ig)}$$

| Comp. No. | R | Z | X | $n_1$ | Y | $R_1$ | $R_2$ | $R_3$ | $R_4$ | $R_5$ | Physical data |
|---|---|---|---|---|---|---|---|---|---|---|---|
| 5.1 | $CF_3$ | H | O | | H | Et | H | H | H | H | 62–64° C. |
| 5.2 | $CF_3$ | H | O | | H | Et | H | H | Me | H | 52–53° C. |
| 5.3 | $CF_3$ | H | O | | H | Et | H | H | Me | Me | |
| 5.4 | $OCF_3$ | H | O | | H | Et | H | H | H | H | |
| 5.5 | —$OCF_2O$— | | O | | H | Et | H | H | H | H | |

TABLE 6

Compounds of the formula Ih $$\text{(Ih)}$$

| Comp. No. | R | Z | X | n | Y | $R_1$ | $R_2$ | $R_3$ | $R_4$ | $R_5$ | Physical data |
|---|---|---|---|---|---|---|---|---|---|---|---|
| 6.1 | $CF_3$ | H | O | | H | Et | H | H | H | H | oil |
| 6.2 | $OCF_3$ | H | O | 1 | 3-Me | Et | H | H | H | H | |
| 6.3 | $CF_3$ | H | O | | H | Et | H | H | Me | H | oil |
| 6.4 | $OCF_3$ | H | O | | H | Et | H | H | Me | H | |

TABLE 7

Compounds of the formula Ile ((−) enantiomers)

$$\text{(Ile)}$$

| Comp. No. | R | Z | X | $R_1$ | Physical data |
|---|---|---|---|---|---|
| 7.1 | $CF_3$ | H | O | $CH_3$ | |
| 7.2 | $CF_3$ | H | O | $C_2H_5$ | $n_D^{22}$ 1.4611 |
| 7.3 | $CF_3$ | H | O | $n\text{-}C_3H_7$ | |
| 7.4 | $CF_3$ | H | O | $i\text{-}C_3H_7$ | |
| 7.5 | $OCF_3$ | H | O | $CH_3$ | |
| 7.6 | $OCF_3$ | H | O | $C_2H_5$ | $n_D^{22}$ 1.4515 |
| 7.7 | $OCF_3$ | H | O | $n\text{-}C_3H_7$ | |
| 7.8 | $OCF_3$ | H | O | $i\text{-}C_3H_7$ | |
| 7.9 | —$OCF_2O$— | | O | $CH_3$ | |
| 7.10 | —$OCF_2O$— | | O | $C_2H_5$ | |

C. BIOLOGICAL EXAMPLES

Example B1

Experimental protocol for pre-emergence herbicidal action Monocotyledon and dicotyledon test plants are sown in standard soil in plastic pots. Immediately after sowing, the test substances are sprayed on in the form of an aqueous suspension prepared with 25% wettable powder (Formulation Example 1) corresponding to a dosage rate of 2 kg of a.i./ha (500 l of water/ha). The test plants are then grown in the greenhouse under optimal conditions. After a test period of 3 weeks, the experiment is evaluated using a nine-step scale (1=complete damage, 9=no action). Scores of 1 to 4 (in particular 1 to 3) mean a good to very good herbicidal action. The same result is obtained using a concentrated wettable powder (Formulation Example 3), dispersible granules (Formulation Example 4), an emulsifiable concentrate (Formulation Example 2) or a suspension concentrate (Formulation Example 6).

Test plants: Setaria, Sinapis, Stellaria

In this experiment, the compounds of the formula I of the examples in Table 1 exhibit a powerful herbicidal action.

Table B1 gives examples of the good herbicidal activity of the compounds of the formula I:

TABLE B1

Pre-emergence action

| Comp. No. | Dosage [kg of a.i./ha] | Setaria | Sinapis | Stellaria | |
|---|---|---|---|---|---|
| 1.1  | 2 | 1 | 1 | 1 | |
| 1.2  | 2 | 1 | 1 | 2 | |
| 1.4  | 2 | 2 | 1 | 1 | |
| 1.5  | 2 | 2 | 1 | 1 | |
| 1.23 | 2 | 3 | 1 | 2 | |
| 1.26 | 2 | 1 | 1 | 1 | |
| 1.27 | 2 | 1 | 1 | 1 | |
| 2.1  | 2 | 2 | 3 | 1 | |
| 2.6  | 2 | 3 | 1 | 2 | (racemate) |
| 2.7  | 2 | 2 | 2 | 1 | (racemate) |
| 2.11 | 2 | 1 | 1 | 1 | |
| 3.1  | 2 | 2 | 2 | 1 | |
| 3.2  | 2 | 3 | 2 | 1 | |
| 3.4  | 2 | 3 | 2 | 1 | |
| 5.2  | 2 | 2 | 2 | 2 | |
| 6.1  | 2 | 1 | 1 | 1 | |
| 6.3  | 2 | 1 | 1 | 1 | |

Example B2

Experimental protocol for post-emergence herbicidal action (contact herbicide) Monocotyledon and dicotyledon test plants are grown in the greenhouse in plastic pots containing standard soil and, in the 4- to 6-leaf stage, sprayed with an aqueous suspension prepared with a 25% wettable powder (Formulation Example 1) of the test substances, corresponding to a dosage rate of 2 kg of a.i./ha (500 l of water/ha). The test plants are then grown in the greenhouse under optimal conditions. After a test period of approximately 18 days, the experiment is evaluated using a nine-step scale (1=complete damage, 9=no action). Scores of 1 to 4 (in particular 1 to 3) mean a good to very good herbicidal action. The same result is obtained using a concentrated wettable powder (Formulation Example 3), dispersible granules (Formulation Example 4), an emulsifiable concentrate (Formulation Example 2) or a suspension concentrate (Formulation Example 6).

Test plants: Setaria, Sinapis, Stellaria

In this experiment, the compounds of the formula I of the examples in Table 1 exhibit a powerful herbicidal action.

Table B2 gives examples of the good herbicidal activity of the compounds of the formula I:

TABLE B2

Post-emergence action

| Comp. No. | Dosage [kg of a.i./ha] | Setaria | Sinapis | Stellaria |
|---|---|---|---|---|
| 1.4  | 2 | 4 | 1 | 4 |
| 1.5  | 2 | 4 | 1 | 4 |
| 1.26 | 2 | 3 | 1 | 3 |
| 2.1  | 2 | 4 | 2 | 4 |
| 2.11 | 2 | 3 | 1 | 4 |
| 6.1  | 2 | 2 | 1 | 2 |
| 6.3  | 2 | 4 | 2 | 3 |

What is claimed is:

1. A compound of formula IIe

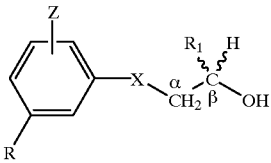

(IIe)

in which

R is halogen, trifluoromethyl, cyano, nitro or $C_1$–$C_3$haloalkoxy;

$R_1$ is $C_1$–$C_5$alkyl;

X is oxygen, sulfur, —SO— or —$SO_2$—;

Z is hydrogen or halogen; or

Z and R together in the 2- and 3-position of the phenyl ring form a group —$OCF_2O$—; and the β-carbon atom is present in optically pure form as the (−) enantiomer.

2. A compound according to claim 1 in which R is chlorine, bromine, trifluoromethyl or trifluoromethoxy; $R_1$ is methyl or ethyl; X is oxygen; and Z is hydrogen or fluorine.

3. A process for the preparation of optically active compounds of the formula IIe

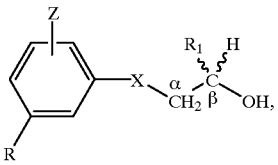

(IIe)

in which R, $R_1$, X and Z are as defined in claim 1 and the β-carbon atom is present in optically pure form as the (−) enantiomer which comprises subjecting the compound of the formula VIII

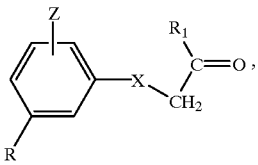

(VIII)

in which R, $R_1$, X and Z are as defined above to a (R)-BINAP/Ru(II)-catalysed hydrogenation reaction in an alcoholic solvent.

* * * * *